(12) United States Patent
Vogelstein et al.

US009970058B2

(10) Patent No.: US 9,970,058 B2
(45) Date of Patent: *May 15, 2018

(54) DIGITAL AMPLIFICATION

(71) Applicant: The Johns Hopkins University, Baltimore, MD (US)

(72) Inventors: Bert Vogelstein, Baltimore, MD (US); Kenneth W. Kinzler, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 503 days.

This patent is subject to a terminal disclaimer.

(21) Appl. No.: 14/512,694

(22) Filed: Oct. 13, 2014

(65) Prior Publication Data

US 2015/0038341 A1    Feb. 5, 2015

Related U.S. Application Data

(60) Division of application No. 13/071,105, filed on Mar. 24, 2011, now Pat. No. 8,859,206, which is a continuation of application No. 12/617,368, filed on Nov. 12, 2009, now Pat. No. 7,915,015, which is a continuation of application No. 11/709,742, filed on Feb. 23, 2007, now Pat. No. 7,824,889, which is a continuation of application No. 10/828,295, filed on Apr. 21, 2004, which is a division of application No. 09/981,356, filed on Oct. 12, 2001, now Pat. No. 6,753,147, which is a continuation of application No. 09/613,826, filed on Jul. 11, 2000, now Pat. No. 6,440,706.

(60) Provisional application No. 60/146,792, filed on Aug. 2, 1999.

(51) Int. Cl.
*C12Q 1/68* (2006.01)

(52) U.S. Cl.
CPC .......... *C12Q 1/6886* (2013.01); *C12Q 1/686* (2013.01); *C12Q 1/6818* (2013.01); *C12Q 1/6851* (2013.01); *C12Q 1/6874* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,213,961 A | 5/1993 | Bunn et al. | |
| 5,518,901 A | 5/1996 | Murtagh | |
| 5,624,819 A | 4/1997 | Skolnick et al. | |
| 5,670,325 A | 9/1997 | Lapidus et al. | |
| 5,677,152 A | 10/1997 | Birch et al. | |
| 5,712,125 A | 1/1998 | Uhlen | |
| 5,736,330 A | 4/1998 | Fulton | |
| 5,736,333 A | 4/1998 | Livak et al. | |
| 5,773,258 A | 6/1998 | Birch et al. | |
| 5,804,383 A | 9/1998 | Gruenert et al. | |
| 5,858,663 A | 1/1999 | Nisson et al. | |
| 5,925,517 A | 7/1999 | Tyagi et al. | |
| 5,928,870 A | 7/1999 | Lapidus et al. | |
| 5,928,907 A | 7/1999 | Woudenberg et al. | |
| 6,020,137 A | 2/2000 | Lapidus et al. | |
| 6,037,130 A | 3/2000 | Tyagi et al. | |
| 6,066,458 A | 5/2000 | Haaland et al. | |
| 6,143,496 A | 11/2000 | Brown et al. | |
| 6,291,163 B1 | 9/2001 | Sidransky | |
| 6,440,706 B1 | 8/2002 | Vogelstein et al. | |

FOREIGN PATENT DOCUMENTS

| | | |
|---|---|---|
| CA | 2075147 | 5/2005 |
| EP | 0643140 A1 | 3/1995 |
| EP | 0747488 A1 | 12/1996 |
| JP | 2001-17179 | 1/2001 |
| WO | 93/18186 | 9/1993 |
| WO | 95/06750 | 3/1995 |
| WO | 9513399 A1 | 5/1995 |
| WO | 95/25429 | 9/1995 |
| WO | 98/08980 | 3/1998 |
| WO | 98/580801 | 12/1998 |
| WO | 9913113 A1 | 3/1999 |
| WO | 99/54510 | 10/1999 |

OTHER PUBLICATIONS

Marras et al., "Multiplex Detection of Single-Nucleotide Variations Using Molecular Beacons," Genetic Analysis: Biomolecular Engineering, Feb. 1999, vol. 14, pp. 151-156.
Whitcomb et al., "Detection of PCR Products Using Self-Proving Amplicons and Fluorescence," Nature Biotechnology, Aug. 1999, vol. 17, pp. 804-807.
Brisco et al., "Detection and Quantitation of Neoplastic Cells in Acute Lymphoblastic Leukemia, by Use of the Polymerase Chain Reaction," British Journal of Haematology, 1991, vol. 79, pp. 211-217.
Notice of Reasons for Rejection issued in Japanese Application No. 2001-513641 and English translation thereof, dated Apr. 28, 2010.
Clairborne, et al. "Theoretical underpinning of the Single-Molecular-Dilution (SMD) Method of Direct Haplotype Resolution," Am. J. Hum. Gen., vol. 46, pp. 1149-1155 (1990).

(Continued)

*Primary Examiner* — Samuel C Woolwine
(74) *Attorney, Agent, or Firm* — Fish & Richardson P.C.

(57) ABSTRACT

The identification of pre-defined mutations expected to be present in a minor fraction of a cell population is important for a variety of basic research and clinical applications. The exponential, analog nature of the polymerase chain reaction is transformed into a linear, digital signal suitable for this purpose. Single molecules can be isolated by dilution and individually amplified; each product is then separately analyzed for the presence of pre-defined mutations. The process provides a reliable and quantitative measure of the proportion of variant sequences within a DNA sample.

11 Claims, 7 Drawing Sheets

(56) References Cited

OTHER PUBLICATIONS

Newton, PCR Essential Data, pp. 51-52, 1995.
Office Action issued in related U.S. Appl. No. 11/709,742, dated Jun. 11, 2010.
Office Action issued in related U.S. Appl. No. 11/709,742, dated Dec. 29, 2009.
Office Action issued in related U.S. Appl. No. 11/709,742, dated Sep. 18, 2009.
Office Action issued in related U.S. Appl. No. 11/709,742, dated Jun. 5, 2009.
Final Office Action issued in related U.S. Appl. No. 90/012,894, dated May 9, 2014.
Final Office Action issued in related U.S. Appl. No. 90/012,895, dated May 9, 2014.
Final Office Action issued in related U.S. Appl. No. 90/012,896, dated May 9, 2014.
Bischoff et al., "Single cell analysis demonstrating somatic mosaicism involving 11p in a patient with a paternal isodisomy and Beckwith-Wiedemann syndrome," Human Molecular Genetics, vol. 4, No. 3, 1995, 395-399.
Kalinina et al, "Nanoliter scale Pcr with TaqMan detection," Nucl. Acids. Res. vol. 25, 1999-2004 (1997).
Chou et al., "Prevention of pre-PCR mis-priming and primer dimerization improves low-copy-number amplifications," Nucleic Acids Res., 20(7):1717-1723 (Apr. 11, 1992).
Burg et al., "Direct and sensitive detection of a pathogenic protozoan, Toxoplasma gondii, by polymerase chain reaction," J. Clin. Microbiol., 27, 1787-1792 (1989).
Trumper et al., "Single-Cell Analysis of Hodgkin and Reed-Sternberg Cells: Molecular Heterogeneity of Gene Expression and p53 Mutations," Blood, 81:3097-3115 (1993).
Kanzler et al., "Molecular Single Cell Analysis Demonstrates the Derivation of Peripheral Blood-Derived Cell Line (L 1236) From the Hodhkin/Reed Sternberg Cells of a Hodgkin's Lymphoma Patient," Blood, 87:3429-3436 (1996).
Gravel et al., "Single-cell analysis of the t(14; 18)(q32; q21) chromosomal translocation in Hodgkin's disease demonstrates the absence of this translocation in neoplastic hodgkin and Reed-Sternberg cells," Blood, 91(8):2866-74 (Apr. 15, 1998).
Ponten et al., "Genomic analysis of single cells from human basal cell cancer using laser-assisted capture microscopy," Mutation Research Genomics 382, 45-55 (1997).
Schwab, "Amplification of oncogenes in human cancer cells," Bioessays 20(6):473-479 (1998).
Non-Final Office Action issued in related U.S. Reexamination Application No. 90/012,894, dated Nov. 27, 2013.
Non-Final Office Action issued in related U.S. Reexamination Application No. 90/012,895, dated Nov. 27, 2013.
Non-Final Office Action issued in related U.S. Reexamination Application No. 90/012,896, dated Nov. 27, 2013.
Jeffreys et al., "Amplification of human minisatellites by the polymerase chain reaction: towards DNA fingerprinting of single cells," Nucl. Acids. Res., vol. 16, No. 23, pp. 10953-10971 (1988).
Supplemental Joint Claim Construction Statement filed in Civil Action No. 12-cv-1173-CCE-JEP on Oct. 28, 2013 (filed with exhibits A, B, and C).
Defendants' Responsive Claim Construction Brief filed in Case No. 1:12-CV-1173 on Nov. 26, 2013.
Deposition of David Sherman, Ph.D., dated Oct. 17, 2013.
Supplemental Joint Claim Construction Statement Exhibit C filed in Civil Action No. 12-cv-1173-CCE-JEP on Oct. 28, 2013 (filed with Supplemental Joint Claim Construction Statement filed in Civil Action No. 12-cv-1173-CCE-JEP on Oct. 28, 2013).
Plaintiffs' Responsive Claim Construction Brief filed in Civil Action No. 12-cv-1173-CCE-JEP on Nov. 26, 2013.
Plaintiffs' Proposed Construction of Disputed Terms, Supporting Evidence, and Rebuttal Evidence Exhibit B, filed in Civil Action No. 12-cv-1173-CCE-JEP on Oct. 28, 2013 (filed with Supplemental Joint Claim Construction Statement filed in Civil Action No. 12-cv-1173-CCE-JEP on Oct. 28, 2013).
Declaration of David H. Sherman in Support of Esoterix Genetic Laboratories' Claim Construction Brief filed in Civil Action Nos. 12-cv-411-CCE-JEP and 12-cv-1173-CCE-JEP, executed Sep. 27, 2013.
Defendants' Opening Claim Construction Brief filed in Case. No. 1:12-CV-1173 on Nov. 5, 2013.
Exhibit A filed in Civil Action No. 12-cv-1173-CCE-JEP on Oct. 28, 2013 (filed with Supplemental Joint Claim Construction Statement filed in Civil Action No. 12-cv-1173-CCE-JEP on Oct. 28, 2013).
Plaintiffs' Opening Claim Construction Brief filed in Civil Action No. 12-cv-1173-CCE-JEP on Nov. 5, 2013.
Examiner Requisition dated Apr. 12, 2013, issued by the Canadian Intellectual Property Office in Canadian Application No. 2,756,675.
Piatek et al, "Molecular beacon sequence analysis for detecting drug resistance in *Mycobacterium tuberculosis*," Nature Biotechnology, 16(4), pp. 359-363, Apr. 1, 1998.
Kruglyak, "Prospects for whole-genome linkage disequilibrium mapping of commin disease genes," Nature Genetics, 22:139-144, Jun. 1999.
Kulozik et al., "Geographical survey of βs-globin gene haplotypes: evidence for an independent Asian origin of the sickle-cell mutation," Am J Hum Gen 39:239-244 (1986).
Irving et al., "TT Virus Infection in Patients with Hepatitis C: Frequency, Persistence, and Sequence Heterogeneity," The Journal of Infectious Diseases, 180:27-34, Jul. 1999.
Simmonds et al., "Human immunodeficiency virus-infected individuals contain provirus in small numbers of peripheral mononuclear cells and at low copy numbers," Journal of Virology, 64(2):864-872 (1990).
Loughlin et al., "Association of the Interleukin-1 Gene Cluster on Chromosome 2q13 With Knee Osteoarthritis," Arthritis & Rheumatism, Jun. 2002, 46(6):1519-1527.
Sykes et al., "Quantitation of Targets for PCR by Use of Limiting Dilution," BioTechniques, 1992, vol. 13, No. 3, pp. 444-449.
Tyagi et al., "Multicolor Molecular Beacons for allele discrimination," Nature Biotechnology, Jan. 1998, vol. 16, No. 1, pp. 303-308.
Vet et al., "Multilex Detection of Four Pathogenic Retroviruses Using Molecular Beacons," Proceedings of the National Academy of Sciences of the United States, May 25, 1999, vol. 96, No. 11, pp. 6394-6399.
Tyagi et al., "Molecular Beacons: proves that Fluoresce Upon Hybridization," Nature Biotechnology, 1996, vol. 14, No. 3, pp. 303-308.
Halford et al., "The Inherent Quantitative Capacity of the Reverse Transcription-Polymerase Chain Reaction," Analytical Biochemistry, Jan. 15, 1999, vol. 266, No. 2, pp. 181-191.
Vogelstein et al., "Digital PCR," Proceedings of the National Academy of Sciences of the United States, Aug. 3, 1999, vol. 96, No. 16, pp. 9236-9241.
Everett et al., "Identification of Nine Species of the Chlamydiaceae Using PCR-RFLP," Int. J. Syst. Bacterial., Apr. 1999, vol. 49, No. 2, pp. 803-813.
Monckton et al., "Minisatellite "Isoallele" Discrimination in Pseudohomozygotes by Single Molecule PCR and Variant Repeat Mapping," Gemonics, 1991, vol. 11, pp. 465-467.
Ruano et al., "Haplotype of Multiple Polymorphisms Resolved by Enzymatic Amplification of Single DNA Molecules," Proc. National Science USA, 1990, pp. 6296-6300.
Navidi et al., "Using PCR in Preimplantation Genetic Desease Diagnosis," Human Reproduction, 1991, vol. 6, No. 6, pp. 836-849.
Li et al., "Amplification and Analysis of DNA Sequences in Single Human Sperm and Diploid Cells," Nature, Sep. 29, 1988, vol. 335, pp. 414-417.
Zhang et al., "Whole Genome Amplification from a Single Cell: Implications for Genetic Analysism," Proc. National Science USA, Jul. 1992, vol. 89, pp. 5847-5851.
Sidransky et al., "Clonal Expansion of p53 Mutant Cells is Associated with Brain Tumour Progression," Nature, Feb. 27, 1992, pp. 846-847.
Jeffreys et al., "Mutation Processes at Human Minisatellites," Electrophoresis, 1995, pp. 1577-1585.

(56) References Cited

OTHER PUBLICATIONS

Schmitt et al., "High Sensitive DNA Typing Approaches for the Analysis of Forensic Evidence: COmparison of Nested Variable Number of Tandem Repeats (VNTR) Amplification and a Short Tandem Repeats (STR) Polymorphism," Forensic Science International, 1994, vol. 66, pp. 129-141.
Lizardi et al., "Mutation Detection and Single-Molecule Counting Using Isothermal Rolling-Circle Amplification," Nature Genetics, Jul. 1998, vol. 19, pp. 225-232.
Parsons et al., "Mismatch Repair Deficiency in Phenotypically Normal Human Cells," Science, May 5, 1995, vol. 268, pp. 738-740.
015 Patent File History Excerpt (response to double patenting rejection) [Response to Office Action, Oct. 6, 2010] 7 pages.
015 Patent Reexamination File History Excerpt (response to rejections adding "isolated") [Response to Final Office Action, dated Jul. 9, 2014] 12 pages.
206 File History Excerpt (rejection over Ruano)[Final Office Action, dated Jun. 27, 2013] 11 pages.
206 File History Excerpt (response to rejection over Ruano) [Response to Final Office Action, dated Sep. 25, 2013] 11 pages.
206 File History Excerpt (response to rejection over Simmonds) [Office Action dated Oct. 10, 2012] 11 pages.
206 File History Excerpt (response to rejection over Simmonds) [Response to Office Action, dated Mar. 11, 2013] 8 pages.
706 Patent File History Excerpt (response rejection over Ruano) [Response to Office Action, dated Jul. 12, 2001] 15 pages.
706 Patent Reexamination File History Excerpt (Lapidus Declaration) [Response to Office Action, dated Sep. 9, 2014] 3 pages.
706 Patent Reexamination File History Excerpt (response to rejections adding "isolated") [Response to Final Office Action, dated Jul. 9, 2014] 18 pages.
706 Patent Reexamination File History Excerpt (Shih Declaration) [Response to Office Action, dated Sep. 9, 2014] 9 pages.
889 Patent File History Excerpt (response to double patenting rejection) (Response to Office Action, dated Apr. 22, 2009] 3 pages.
*Amneal Pharmaceuticals, LLC v. Supernus Pharmaceuticals. Inc.*, IPR2013-00368, Paper No. 8 (Dec. 17, 2013), 15 pages.
Ananthaswamy et al., "Inhibition of Solar Siinulator-Induced p53 Mutations and Protection Against Skin Cancer Development in Mice by Sunscreens," *The Journal of Investigative Dermatology*, 112:763-768, 1999.
Andrew Leigh Brown and Peter Simmonds, Sequence analysis of virus variability based on the poymerase (sic) chain reaction (PCR). Chapter 11 of 1 HIV: A Practical Approach, Jonathan Karn, Ed. (1995), 30 pages.
Bar-Eli et al., "Analysis of N-RAS Exon-1 Mutations in Myelodysplastic Syndromes by Polymerase Chain Reaction and Direct Sequencing," *Blood*, vol. 73. No. 1 Jan. 1989: pp. 281-283.
Birch et al., Simplified hot start PCR, Nature 381:445-446 (1996).
Bos et al., "Prevalence of ras gene mutations in human colorectal cancers," *Nature* vol. 328 May 1987. pp. 293-297.
Brossart et al., "A Polymerase Chain Reaction-based Semi quantitative Assessment of Malignant Melanoma Cells in Peripheral Blood," *Cancer Research* 55, 4065-4068. Sep. 15, 1995.
Carteau et al., Chromosome structure and human immunodeficiency virus type 1 cDNA integration: Centromeric alphoid repeats are a disfavored target, Journal of Immunology 72:4005-4014 (1998).
Chapter 6 of PCR: The Polymerase Chain Reaction 67-88, Kary B. Mullis, Francois Ferre, and Richard A. Gibbs Eds. (1994).
Chen et al., "A Nonradioactive, Allele-Specific Polymerase Chain Reaction for Reproducible Detection of Rare Mutations in Large Amounts of Genomic DNA: Application to Human k-ras," Analytical Biochemistry 244 pp. 191-194 (1997).
Chen et al., "Fluorescence Polarization Honlogeneous Nucleic Acid Analysis," *Genome Research*, pp. 492-498 (1999).
Chiang et al., "Use of a Fluorescent-PCR Reaction to Detect Genomic Sequence Copy Number and Transcriptional Abundance," *Genome Research*, 6:1013-1026, 1996, 15 pages.

Coffin, HIV population dynamics in vivo: Implications for genetic variation, pathogenesis and therapy, *Science* 267:483-489 (1995).
Collins et al., "Rare Occurrence of N-ras Point Mutations in Philadelphia Chromosome Positive Chronic Myeloid Leukemia," Blood, vol. 73, No. 4 Mar. 1989: pp. 1028-1032.
Complaint, *Esoterix Genetic Laboratories, LLC and The Johns Hopkins University v. Myriad Genetics, Inc. et al.*, 16-cv-1112, D.I. 1 (M.D.N.C. Sep. 7, 2016), 19 pages.
Cortopassi et al., "Detection of a specific mitochondrial DNA deletion in tissues of older humans," *Nucleic Acids Research*, vol. 18, No. 23 6927-6933, 1990.
Cortopassi et al., "Using the polymerase chain reaction to estimate mutation frequencies and rates in human cells.," *Mutation Research*, 277 (1992) 239-249.
Curriculum Vitae of Gregory Allen Buck, dated Aug. 2017, 24 pages.
Curriculum Vitae of Michael L. Metzker, Ph.D., 18 pages, filed Mar. 16, 2017 for IPR2017-01102.
Day et al., "Digital PCR strategies in the development and analysis of molecular biomarkers for personalized medicine," *Methods* 59 (2013) 101-107.
Day et al., "Nucleotide analogs and new buffers improve a generalized method to enrich for low abundance mutations," *Nucleic Acids Research*, 1999, vol. 27, No. 8 1819-1827.
Declaration of Bhanu K. Sadasivan in Support of Defendant Ambry Genetics Corporation's Opening Claim Construction Brief, Civil Action No. 16-CV-1111, Filed Sep. 7, 2017, 218 pages.
Declaration of Gregory A Buck. Ph.D, Inter Partes Review of U.S. Pat. No. 6,440,706, IPR 2017-02086, 63 pages, dated Sep. 10, 2017.
Declaration of Michael L. Metzker, Ph.D. Inter Partes Review of U.S. Pat. No. 6,440,706, 189 pages, dated Mar. 16, 2017.
Declaration of Robin A. Adkins in Support of Esoterix Genetic Laboratories, LLC's and The Johns Hopkins University's Opening Claim Construction Brief, Case No. 1:16-cv-11.11-WO-JEP, Filed Sep. 7, 2017, 237 pages.
Defendant Ambry Genetics Corporation's Opening Claim Construction Brief, Civil Action No. 16-CV-1111, Filed Sep. 7. 2017, 43 pages.
Defendant Ambry Genetics Corporation's Responsive Claim Construction Brief Civil Action No. 16-CV-1111 WO (JEP), Filed Oct. 5, 2017, 31 pages.
Defendants Myriad Genetics, Inc. and Myriad Genetic Laboratories, Inc.'s Preliminary Non-Infringement and Patent Invalidity Contentions Pursuant to Local Patent Rule 103.3 Filed in Case No. 1.16--CV-1112, May 4, 2017, 33 pages.
Dicker et al., "Mutational Analysis of Human NRAS Genes in Malignant Melanoma: Rapid Methods for Oligonucleotide Hybridization and Manual and Automated Direct Sequencing of Products Generated by the Polymerase Chain Reaction," Genes, Chromosomes & Cancer 1:257-269 (1990).
*Esoterix Genetic Laboratories, LLC and The Johns Hopkins University v. Ambry Genetics Corporation*, "Complaint for Patent Infringement" Civil Action No. 16-cv-1111, Sep. 7, 2016, 19 pages.
Ex Parte Reexamination Certificate, U.S. Pat. No. 6,440,706 Certificate Issued Oct. 24, 2014, 2 pages.
Ex Parte Reexamination File History for U.S. Pat. No. 6,440,706, (re-exam filed Jun. 17, 2103).
Ex Parte Reexamination File History for U.S. Pat. No. 7,824,889, (re-exam filed Jun. 17, 2013).
Ex Parte Reexamination File History for U.S. Pat. No. 7,915,015, (re-exam filed Jun. 17, 2013).
Fearon and Vogelstein,A Genetic Mode/for Colorectal Tumorigenesis, Cell 61, 759-767 (1990).
Gibson et al., "A homogeneous method for genotyping with fluorescence polarization," Clinical Chemistry 43:8 pp. 1336-1341 (1997).
Haliassos et al., Detection of minority point mutations by modified PCR technique: a new approach for a sensitive diagnosis of tumor-progression markers, *Nucleic Acids Research*, vol. 17 No. 20 1989.
Haque et al., "Anlplification Refractory Mutation Systetn Linear Extension: A Novel, Gel-Free, Enzyme-Linked Immunoassay Method for .DNA Genotyping," *Diagn mol pathol* 7(5): 248-252, 1998.

(56) References Cited

OTHER PUBLICATIONS

Hayashi et al., "Genetic Diagnosis Identities Occult Lymph Node Metastases Undetectable by the Histopathological Method," Cancer Research 54, 3853-3856, Jul. 15, 1994.
Heid et al., Real time quantitative PCR, Genome Research 6:986-994 (1996).
Ho et al., Rapid turnover of plasma virions and CD4 lyniphocyte in HIV-1 infection, *Nature* 373:123-126 (1995).
Hochhaus et al., "Quantification of Residual Disease its Chronic Myelogenous Leukemia Patients on Interferon-a Therapy by Competitive Polymerase Chain Reaction," *Blood*, vol. 87, No. 4 Feb. 15, 1996: pp. 1549-1555.
International Preliminary Report on Patentability in International Application No. PCT/US00/20740, dated Apr. 30, 2002, 8 pages.
International Search Report in International Application No. PCT/US00/20740, dated Dec. 21, 2001, 4 pages.
Jonason et al., "Frequent clones of p53-mutated keratinocytes in normal human skin," *PNAS* vol. 93, pp. 14025-14029, Nov. 1996.
Kahn et al., "Diagnostic Detection of Mutant ras Genes in Minor Cell Populations," Methods in Enzymology. vol. 255, pp. 452-464, (1995).
Kellogg et al., TaqStart Antibody: 'Hot Start' PCR Facilitated by a Neutralizing Monoclonal Antibody Directed Against Taq DNA Polymerase, Biotechniques 16 (6):1134-1136 (1994).
Koch et al., "p53 Gene Mutations as Markers of Tumor Spread in Synchronous Oral Cancers," Arch Otolaryngol HFAD Neck Surg vol. 120, SFP 1994, pp. 943-947.
Kumar et al., "Activation of ras Oncogenes Preceding the Onset of Neoplasia," *Science*, Jun. 1, 1990; 248, pp. 1101-1104.
Laken et al., "Genotyping by mass spectrometric analysis of short DNA fragments," Nature Biotechnology vol. 16 Dec. 1998, pp. 1352-1356.
Lee et al., "Allelic discrimination by nick-translation PCR with fluorogenic probes," Nucleic Acids Research, 1993, vol. 21, No. 16 3761-3766.
Levinson et al., "Molecular Characterization of Transgene-induced Immunodeficiency in B-less Mice Using a Novel Quantitative Limiting Dilution Polymerase Chain Reaction Method," J. Exp. Med, vol. 178, Jul. 1993, pp. 317-329.
Levran et al., "Sequence variation in the Fanconi anemia gene FAA," Proc. Natl. Acad. Sci USA, vol. 94, pp. 13051-13056 Nov. 1997.
Mao et al., "Detection of Oncogene Mutations in Sputum Precedes Diagnosis of Lung Cancer," *cancer Research* 54, 1634-1637 Apr. 1, 1994.
Monya Baker, Digital PCR hits its stride, Nature Methods 9 (6):541-544 (2012).
Morley, "Digital PCR: A brief history" Biomolecular Detection and Quantification 1 (2014) 1-2.
Mullis et al., The Polymerase Chain Reaction, 1994, 24 pages.
Myriad Answer, Affirmative Defenses, and Counterclaims, *Esoterix Genetic Laboratories, LLC and The Johns Hopkins University* v. *Myriad Genetics, Inc. et al.*, 16-cv-1112, D.I. 22 (M.D.N.C. Nov. 2, 2016).
Navidi et al.. "A Multiple-tubes Approach fo Accurate Genotyping of very small DNA Samples by Using PCR: Statistical Considerations," *Am J. Hum Genet* 50:347-359, 1992.
Nawroz et al., "Microsatellite alterations in serum DNA of head and neck cancer patients," *Nature Medicine*, vol. 2, No. 9, Sep. 1996, pp. 1035-1037.
Ozawa, "Genetic and Functional Changes in Mitochondria Associate with aging," *Psychological Review*, vol. 77 No. 2 Apr. 1997, pp. 425-464.
Paris et al., "Probing DNA sequences in solution with a monomer-excimer fluorescence color change," *Nucleic Acids Research*, 1998, vol. 26. No. 16 3789-3793.
Perelson et al., HIV-1 dynamics in vivo: virion clearance rate. infected cell life-span, and viral generation time, Science, 271:1582-1586 (1996).

Petition for Inter Partes Review of U.S. Pat. No. 6,440,706 IPR 2017-01102, dated Mar. 16, 2017.
Petition for Inter Partes Review of U.S. Pat. No. 6,440,706 IPR 2017-02086, dated Sep. 10, 2017.
Petition for Inter Partes Review of U.S. Pat. No. 7,824,889 IPR 2017-01106, dated Mar. 16, 2017.
Petition for Inter Partes Review of U.S. Pat. No. 7,824,889 IPR 2017-02093, dated Sep. 10, 2017.
Petition for Inter Partes Review of U.S. Pat. No. 7,915,015 IPR 2017-011107, dated Mar. 16, 2017.
Petition for Inter Partes Review of U.S. Pat. No. 7,915,015 IPR 2017-02095, dated Sep. 10, 2017.
Petition for Inter Partes Review of U.S. Pat. No. 8,859,206 IPR 2017-01105, dated Mar. 16, 2017.
Petition for Inter Partes Review of U.S. Pat. No. 8,859,206 IPR 2017-02096, dated Sep. 10, 2017.
Plaintiffs Esoterix Genetic Laboratories, LLC's and The John Hopkins University's Opening Claim Construction Brief, Case No. 1:16-cv-1111-WO-JEP, Filed Sep. 7, 2017, 51 pages.
Plaentiffs Esoterix Genetic Laboratories, LLC's and The Johns Hopkins University's Responsive Claim Construction Brief, 16-cv-1111-WO-JEP, Filed Oct. 5, 2017, 46 pages.
Plaintiffs' Proposed Constructions of Disputed Terms, Supporting Evidence, and Rebuttal Evidence Exhibit B in Civil Action No. 1:16-cv-1111 *Esoterix Genetic Laboratories, LLC and The Johns Hopkins University* v. *Ambry Genetics Corporation*, Filed Jul. 24, 2017, 79 pages.
U.S. Appl. No. 60/146,792, filed Aug. 2, 1999, 37 pages.
R.W. Old, Principles of Gene Manipulation an Introduction to genetic Engineering, Studies in Microbiology Fifth Edition, 1994. pp. 178-190.
Reexamination Request for U.S. Pat. No. 6,440,706, dated Jun. 27, 2013, 544 pages.
Saiki et al., "Analysis of enzymatically amplified b-globin an dHLA-Dqa DNA with allele-specific oligonucleotide probes," *Letters to Nature*, vol. 324 13 pp. 163-166, Nov. 1986.
Saiki et al., "Primer-Directed Enzymatic Amplification of DNA with a Thermostable DNA Polymerase," *Reports* pp. 487-491, Jan. 29, 1988, 5 pages.
Sidransky et al., "Identification of p53 Gene Mutations in Bladder Cancers and Urine Samples," Science; May 3, 1991; 252, 5006, pp. 706-709.
Sidransky et al., Identification of ras Oncogene Mutations in the Stool of Patients with Curable Colorectal Tumors, Science; Apr. 3, 1992; 256. 5053, pp. 102-105.
Sidransky et al., "Nucleic Acid-Based Methods for the Detection of Cancer," Science; Nov. 7, 1997; 278, 5340 pp. 1054-1058.
Smith-Raven et al., "Detection of c-Ki-ras mutations in faecal samples from sporadic colorectal cancer patients," *Gut* 1995; 36: 81-86.
Supplemental Declaration of Bhanu K. Sadasivan in Support of Defendant Ambry Genetics Corporation's Responsive Claim Construction Brief, Civil Action No. 16-CV-1111, Oct. 5, 2017, 31 pages.
Sykes et al., Limiting dilution polymerase chain reaction. chapter 8 of Reverse Transcriptase PCR, Larrick and Siebert, Eds. (1995).
Szollosi et al., "Application of Fluorescence Resonance Energy Transfer in the Clinical Laboratory: Routine and Research," Cytometry 34:159-179 (1998).
Taberlet et al., "Reliable genotyping of samples with very low DNA quantities using PCR," *Nucleic Acids Research*, 1996, vol. 24. No. 16 3189-3194.
Tada et al., "Detection of ras Gene Mutations in Pancreatic Juice and Peripheral Blood of Patients with Pancreatic Adenocarcinoma," *Cancer Research* 53, 2472-2474, Jun. 1, 1993.
Termination Dismissing the Proceeding issued in IPR2017-01102 (U.S. Pat. No. 6,440,706 B1) Case IPR2017-01105 (U.S. Pat. No. 8,859,206 B2) Case IPR2017-01106 (U.S. Pat. No. 7,824,889 B2) Case IPR2017-01107 (U.S. Pat. No. 7,915,015 B2), dated Aug. 22, 2017.
Vogelstein et al., "Allelotype of Colorectal Carcinomas," Science; Apr. 14, 1989; 244, 4901, pp. 207-211.

(56) References Cited

OTHER PUBLICATIONS

Wei et al., Viral dynamics in human immunodeficiency virus type 1 infection, *Nature*, 373:117-122 (1995).
Whitcombe et al., "Advances in approaches to DNA-based diagnostics," *Pharmaceutical biotechnology*, 1998, 9:602-608.
Zacher et al., "Absolute quantification of target DNA: a simple competitive PCR for efficient analysis of multiple samples," Nucleic Acids Research, 1993, vol. 21, No. 8 2017-2018.
Zimmermann et al., Digital PCR: a powerful new tool for for noninvasive prenatal diagnosis? Prenatal Diagnosis 28:1087-1093 (2008).

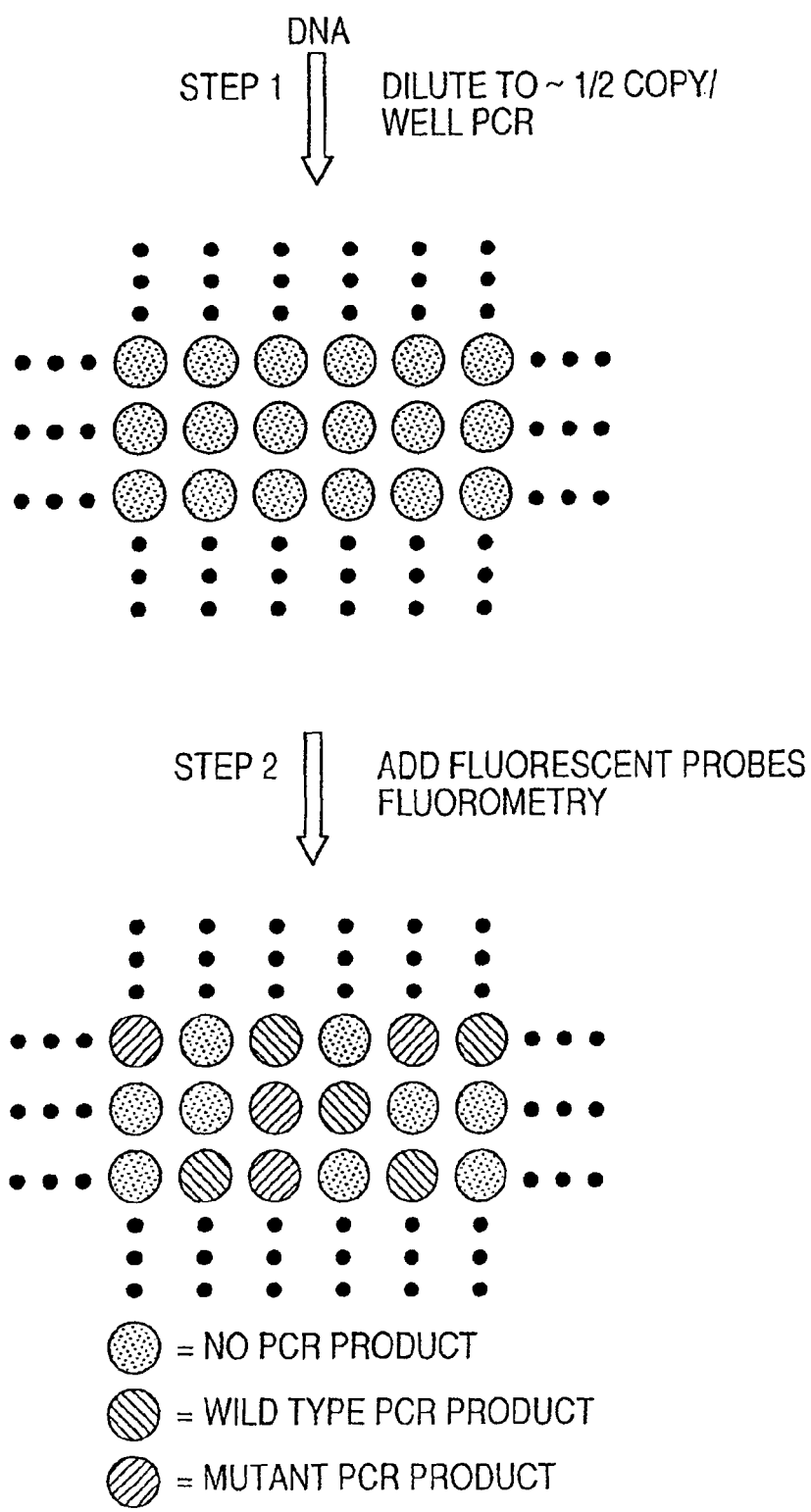

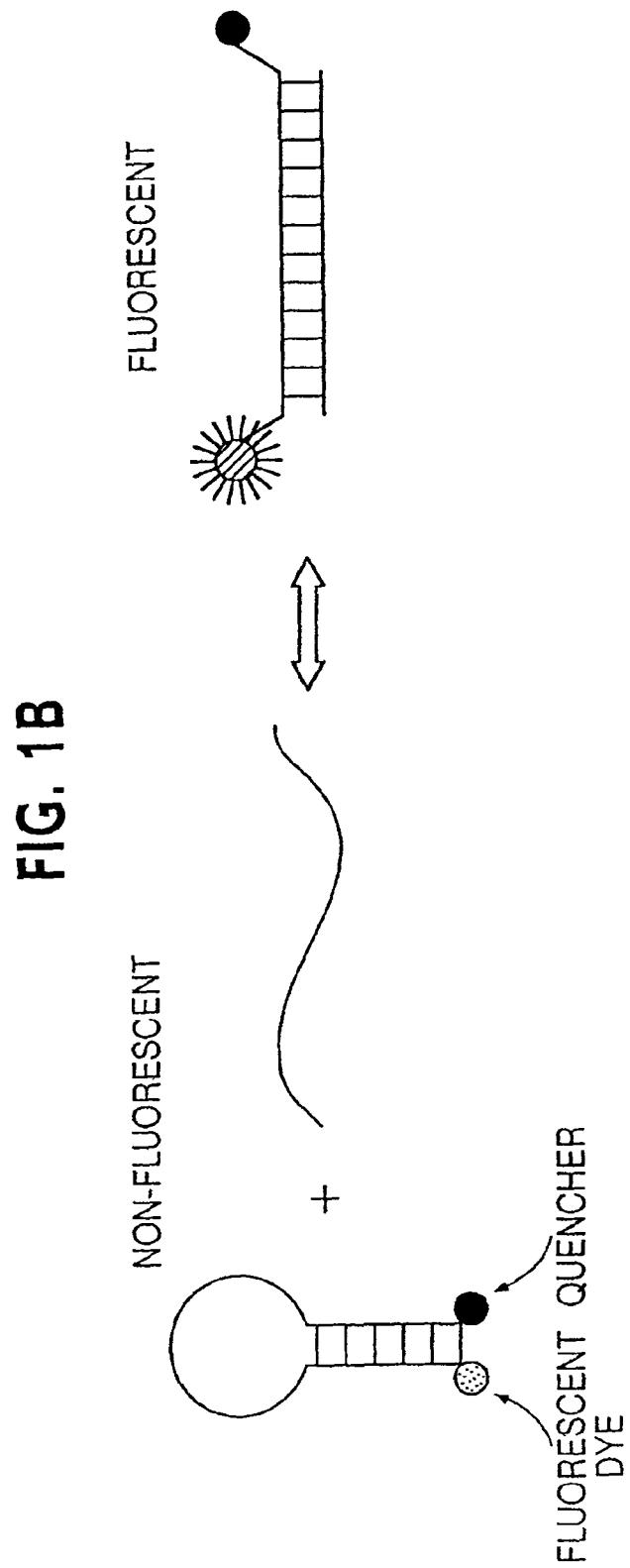

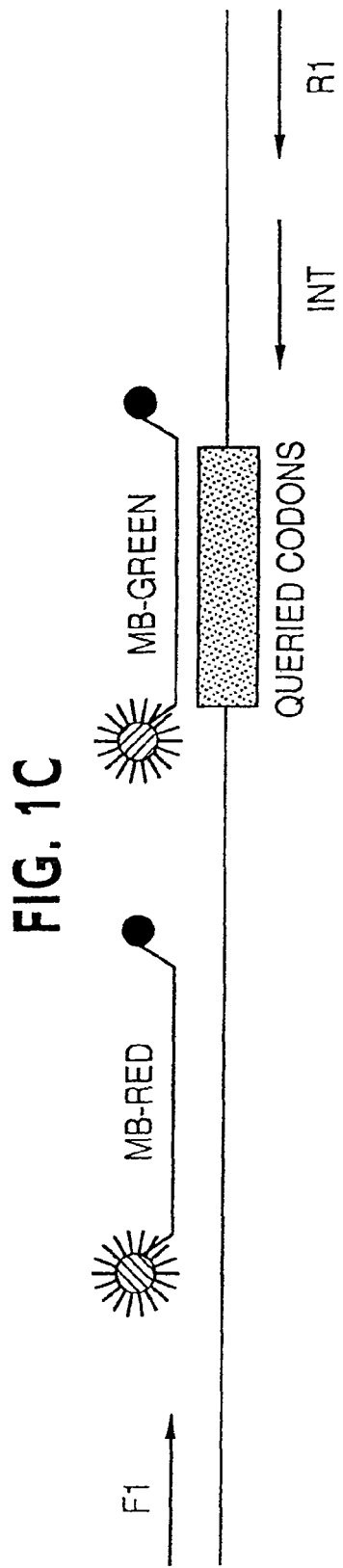

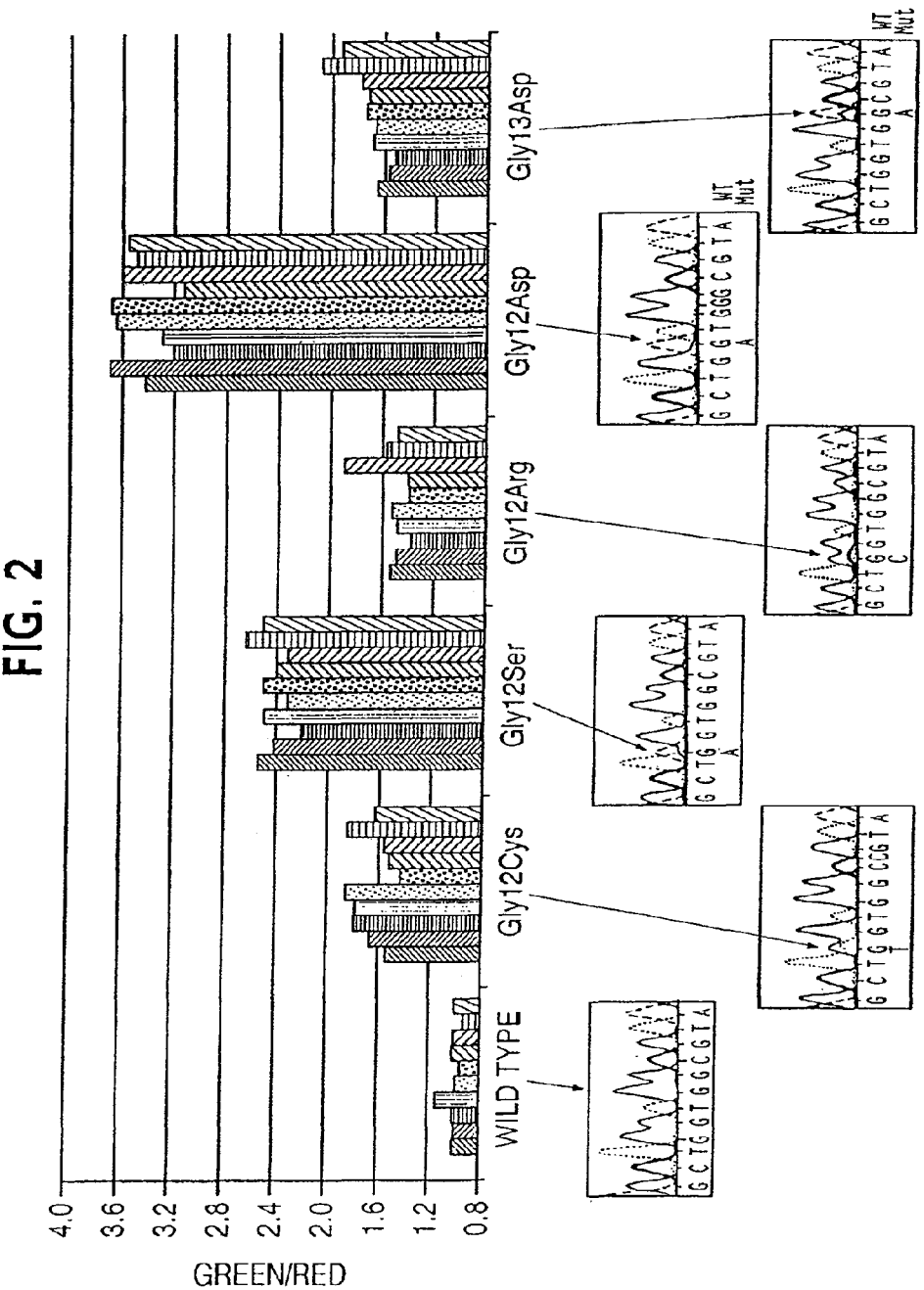

DIGITAL AMPLIFICATION

The U.S. government retains certain rights in this invention by virtue of its support of the underlying research, supported by grants CA 43460, CA 57345, and CA 62924 from the National Institutes of Health.

The disclosure of all claimed priority applications is expressly incorporated herein.

TECHNICAL FIELD OF THE INVENTION

This invention is related to diagnostic genetic analyses. In particular it relates to detection of genetic changes and gene expression.

BACKGROUND OF THE INVENTION

In classical genetics, only mutations of the germ-line were considered important for understanding disease. With the realization that somatic mutations are the primary cause of cancer, and may also play a role in aging, new genetic principles have arisen. These discoveries have provided a wealth of new opportunities for patient management as well as for basic research into the pathogenesis of neoplasia. However, many of these opportunities hinge upon detection of a small number of mutant-containing cells among a large excess of normal cells. Examples include the detection of neoplastic cells in urine, stool, and sputum of patients with cancers of the bladder, colorectum, and lung, respectively. Such detection has been shown in some cases to be possible at a stage when the primary tumors are still curable and the patients asymptomatic. Mutant sequences from the DNA of neoplastic cells have also been found in the blood of cancer patients. The detection of residual disease in lymph nodes or surgical margins may be useful in predicting which patients might benefit most from further therapy. From a basic research standpoint, analysis of the early effects of carcinogens is often dependent on the ability to detect small populations of mutant cells.

Because of the importance of this issue in so many settings, many useful techniques have been developed for the detection of mutations. DNA sequencing is the gold standard for the detection of germ line mutations, but is useful only when the fraction of mutated alleles is greater than ~20%. Mutant-specific oligonucleotides can sometimes be used to detect mutations present in a minor proportion of the cells analyzed, but the signal to noise ratio distinguishing mutant and wild-type (WT) templates is variable. The use of mutant-specific primers or the digestion of polymerase chain reaction (PCR) products with specific restriction endonucleases are extremely sensitive methods for detecting such mutations, but it is difficult to quantitate the fraction of mutant molecules in the starting population with these techniques. Other innovative approaches for the detection of somatic mutations have been reviewed. A general problem with these methods is that it is difficult or impossible to independently confirm the existence of any mutations that are identified.

Thus there is a need in the art for methods for accurately and quantitatively detecting genetic sequences in mixed populations of sequences.

SUMMARY OF THE INVENTION

It is an object of the present invention to provide methods for determining the presence of a selected genetic sequence in a population of genetic sequences.

It is another object of the present invention to provide molecular beacon probes useful in the method of the invention.

These and other objects of the invention are achieved by providing a method for determining the presence of a selected genetic sequence in a population of genetic sequences. A biological sample comprising nucleic acid template molecules is diluted to form a set of assay samples. The template molecules within the assay samples are amplified to form a population of amplified molecules in the assay samples of the set. The amplified molecules in the assay samples of the set are then analyzed to determine a first number of assay samples which contain the selected genetic sequence and a second number of assay samples which contain a reference genetic sequence. The first number is then compared to the second number to ascertain a ratio which reflects the composition of the biological sample.

Another embodiment of the invention is a method for determining the ratio of a selected genetic sequence in a population of genetic sequences. Template molecules within a set comprising a plurality of assay samples are amplified to form a population of amplified molecules in each of the assay samples of the set. The amplified molecules in the assay samples of the set are analyzed to determine a first number of assay samples which contain the selected genetic sequence and a second number of assay samples which contain a reference genetic sequence. At least one-fiftieth of the assay samples in the set comprise a number (N) of molecules such that 1/N is larger than the ratio of selected genetic sequences to total genetic sequences required to determine the presence of the selected genetic sequence. The first number is compared to the second number to ascertain a ratio which reflects the composition of the biological sample.

According to another embodiment of the invention, a molecular beacon probe is provided. It comprises an oligonucleotide with a stem-loop structure having a photoluminescent dye at one of the 5' or 3' ends and a quenching agent at the opposite 5' or 3' end. The loop consists of 16 base pairs which has a $T_m$ of 50-51 C. The stem consists of 4 base pairs having a sequence 5'-CACG-3'.

A second type of molecular beacon probe is provided in another embodiment. It comprises an oligonucleotide with a stem-loop structure having a photoluminescent dye at one of the 5' or 3' ends and a quenching agent at the opposite 5' or 3' end. The loop consists of 19-20 base pairs and has a $T_m$ of 54-56 C. The stem consists of 4 base pairs having a sequence 5'-CACG-3'.

Another embodiment provides the two types of molecular beacon probes, either mixed together or provided in a divided container as a kit.

The invention thus provides the art with the means to obtain quantitative assessments of particular DNA or RNA sequences in mixed populations of sequences using digital (binary) signals.

BRIEF DESCRIPTION OF THE DRAWINGS

FIG. 1A, 1B, 1C. Schematic of experimental design. (FIG. 1A) The basic two steps involved: PCR on diluted DNA samples is followed by addition of fluorescent probes which discriminate between WT and mutant alleles and subsequent fluorometry. (FIG. 1B) Principle of molecular beacon analysis. In the stem-loop configuration, fluorescence from a dye at the 5' end of the oligonucleotide probe is quenched by a Dabcyl group at the 3' end. Upon hybridization to a template, the dye is separated from the quencher, resulting in increased fluorescence. Modified from Marras et al. (FIG. 1C) Oligonucleotide design. Primers F1 and R1 are used to amplify the genomic region of interest. Primer INT is used to produce single stranded DNA from the original PCR products during a subsequent asymmetric PCR step (see Materials and Methods). MB-RED is a Molecular Beacon which detects any appropriate PCR product, whether it is WT or mutant at the queried codons. MB-GREEN is a Molecular Beacon which preferentially detects the WT PCR product.

FIG. 2. Discrimination between WT and mutant PCR products by Molecular Beacons. Ten separate PCR products, each generated from ~25 genome equivalents of genomic DNA of cells containing the indicated mutations of c-Ki-Ras, were analyzed with the Molecular Beacon probes described in the text. Representative examples of the PCR products used for Molecular Beacon analysis were purified and directly sequenced. In the cases with Gly12Cys (SEQ ID NO: 11) and Gly12Arg (SEQ ID NO: 10) mutations, contaminating non-neoplastic cells within the tumor presumably accounted for the relatively low ratios. In the cases with Gly12Ser (SEQ ID NO: 8) and Gly12Asp (SEQ ID NO: 12), there were apparently two or more alleles of mutant c-Ki-Ras for every WT allele (SEQ ID NO: 7); both these tumors were aneuploid. Analysis of the Gly13Asp mutation is also shown (SEQ ID NO: 9).

DETAILED DESCRIPTION OF THE INVENTION

Figure 3:
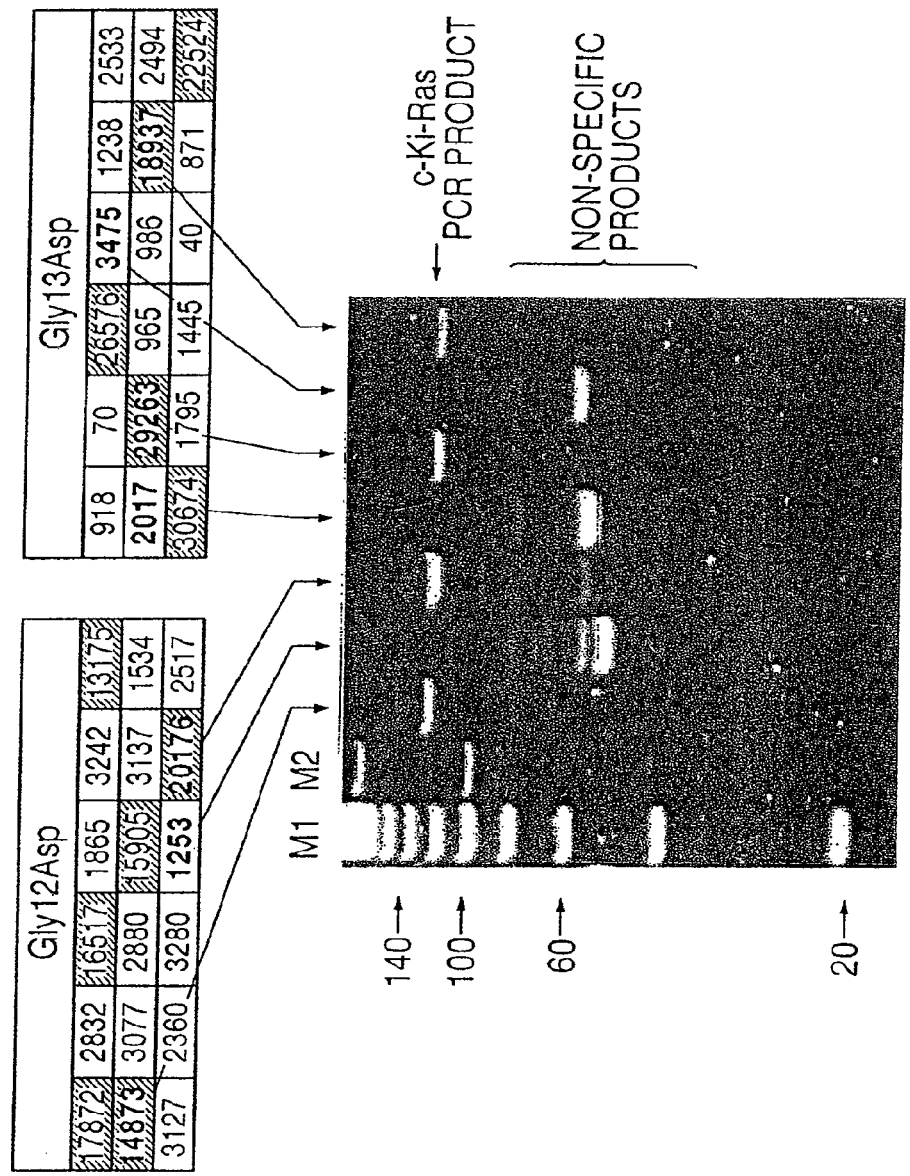
FIG. 3. Detecting Dig-PCR products with MB-RED. Specific Fluorescence Units of representative wells from an experiment employing colorectal cancer cells with Gly12Asp or Gly13Asp mutations of the c-Ki-Ras gene. Wells with values >10,000 are shaded yellow. Polyacrylamide gel electrophoretic analyses of the PCR products from selected wells are shown. Wells with fluorescence values <3500 had no PCR product of the correct size while wells with fluorescence values >10,000 SFU always contained PCR products of 129 bp. Non-specific products generated during the large number of cycles required for Dig-PCR did not affect the fluorescence analysis. M1 and M2 are molecular weight markers used to determine the size of fragments indicated on the left (in base pairs).

The method devised by the present inventors involves separately amplifying small numbers of template molecules so that the resultant products have a proportion of the analyte sequence which is detectable by the detection means chosen. At its limit, single template molecules can be amplified so that the products are completely mutant or completely wild-type (WT). The homogeneity of these amplification products makes them trivial to distinguish through existing techniques.

The method requires analyzing a large number of amplified products simply and reliably. Techniques for such assessments were developed, with the output providing a digital readout of the fraction of mutant alleles in the analyzed population.

The biological sample is diluted to a point at which a practically usable number of the diluted samples contain a proportion of the selected genetic sequence (analyte) relative to total template molecules such that the analyzing technique being used can detect the analyte. A practically usable number of diluted samples will depend on cost of the analysis method. Typically it would be desirable that at least $1/50$ of the diluted samples have a detectable proportion of analyte. At least $1/10$, $1/5$, $3/10$, $2/5$, $1/2$, $3/5$, $7/10$, $4/5$, or $9/10$ of the diluted samples may have a detectable proportion of analyte. The higher the fraction of samples which will provide useful information, the more economical will be the overall assay. Over-dilution will also lead to a loss of economy, as many samples will be analyzed and provide no signal. A particularly preferred degree of dilution is to a point where each of the assay samples has on average one-half of a template. The dilution can be performed from more concentrated samples. Alternatively, dilute sources of template nucleic acids can be used. All of the samples may contain amplifiable template molecules. Desirably each assay sample prior to amplification will contain less than a hundred or less than ten template molecules.

Digital amplification can be used to detect mutations present at relatively low levels in the samples to be analyzed. The limit of detection is defined by the number of wells that can be analyzed and the intrinsic mutation rate of the polymerase used for amplification. 384 well PCR plates are commercially available and 1536 well plates are on the horizon, theoretically allowing sensitivities for mutation detection at the ~0.1% level. It is also possible that Digital Amplification can be performed in microarray format, potentially increasing the sensitivity by another order of magnitude. This sensitivity may ultimately be limited by polymerase errors. The effective error rate in PCR as performed under our conditions was 1.1%, i.e., four out of 351 PCR products derived from WT DNA sequence appeared to contain a mutation by RED/GREEN ratio criteria. However, any individual mutation (such as a G to T transversion at the second position of codon 12 of c-Ki-Ras), are expected to occur in <1 in 50 of these polymerase-generated mutants (there are at least 50 base substitutions within or surrounding codons 12 and 13 that should yield high RED/GREEN ratios). Determining the sequence of the putative mutants in the positive wells, by direct sequencing as performed here or by any of the other techniques, provides unequivocal validation of a prospective mutation: a significant fraction of the mutations found in individual wells should be identical if the mutation occurred in vivo. Significance can be established through rigorous statistical analysis, as positive signals should be distributed according to Poisson probabilities. Moreover, the error rate in particular Digital Amplification experiments can be precisely determined through performance of Digital Amplification on DNA templates from normal cells.

Digital Amplification is as easily applied to RT-PCR products generated from RNA templates as it is to genomic DNA. For example, the fraction of alternatively spliced or mutant transcripts from a gene can be easily determined using photoluminescent probes specific for each of the PCR products generated. Similarly, Digital Amplification can be used to quantitate relative levels of gene expression within an RNA population. For this amplification, each well would contain primers which are used to amplify a reference transcript expressed constitutively as well as primers specific for the experimental transcript. One photoluminescent probe would then be used to detect PCR products from the reference transcript and a second photoluminescent probe used for the test transcript. The number of wells in which the test transcript is amplified divided by the number of wells in which the reference transcript is amplified provides a quantitative measure of gene expression. Another group of examples involves the investigations of allelic status when two mutations are observed upon sequence analysis of a standard DNA sample. To distinguish whether one variant is present in each allele (vs. both occurring in one allele), cloning of PCR products is generally performed. The approach described here would simplify the analysis by eliminating the need for cloning. Other potential applications of Digital Amplification are listed in Table 1. When the goal is the quantitation of the proportion of two relatively common alleles or transcripts rather than the detection of rare alleles, techniques such as those employing TaqMan and real time PCR provide an excellent alternative to use of molecular beacons. Advantages of real time PCR methods include their simplicity and the ability to analyze multiple samples simultaneously. However, Digital Amplification may prove useful for these applications when the expected differences are small, (e.g., only ~2-fold, such as occurs with allelic imbalances.)

In one preferred embodiment each diluted sample has on average one half a template molecule. This is the same as one half of the diluted samples having one template molecule. This can be empirically determined by amplification. Either the analyte (selected genetic sequence) or the reference genetic sequence can be used for this determination. If the analysis method being used can detect analyte when present at a level of 20%, then one must dilute such that a significant number of diluted assay samples contain more than 20% of analyte. If the analysis method being used requires 100% analyte to detect, then dilution down to the single template molecule level will be required.

To achieve a dilution to approximately a single template molecule level, one can dilute such that between 0.1 and 0.9 of the assay samples yield an amplification product. More preferably the dilution will be to between 0.1 and 0.6, more preferably to between 0.3 and 0.5 of the assay samples yielding an amplification product.

The digital amplification method requires analysis of a large number of samples to get meaningful results. Preferably at least ten diluted assay samples are amplified and analyzed. More preferably at least 15, 20, 25, 30, 40, 50, 75, 100, 500, or 1000 diluted assay samples are amplified and analyzed. As in any method, the accuracy of the determination will improve as the number of samples increases, up to a point. Because a large number of samples must be analyzed, it is desirable to reduce the manipulative steps, especially sample transfer steps. Thus it is preferred that the steps of amplifying and analyzing are performed in the same receptacle. This makes the method an in situ, or "one-pot" method.

The number of different situations in which the digital amplification method will find application is large. Some of these are listed in Table 1. As shown in the examples, the method can be used to find a tumor mutation in a population of cells which is not purely tumor cells. As described in the examples, a probe for a particular mutation need not be used, but diminution in binding to a wild-type probe can be used as an indicator of the presence of one or more mutations. Chromosomal translocations which are characteristic of leukemias or lymphomas can be detected as a measure of the

| Application | Example | Probe 1 Detects: | Probe 2 Detects: |
| --- | --- | --- | --- |
| Base substitution mutations | Cancer gene mutations in stool, blood, lymph nodes | mutant or WT alleles | WT PCR products |
| Chromosomal translocations | Residual leukemia cells after therapy (DNA or RNA) | normal or translocated alleles | translocated allele |
| Gene amplifications | Determine presence or extent of amplification | sequence within amplicon | sequence from another part of same chromosome arm |
| Alternatively spliced products | Determine fraction of alternatively spliced transcripts from same gene (RNA) | minor exons | common exons |
| Changes in gene expression | Determine relative levels of expression of two genes (RNA) | first transcript | reference transcript |
| Allelic discrimination | Two different alleles mutated vs. one mutation in each of two alleles | first mutation | second mutation |
| Allelic Imbalance | Quantitative analysis with non-polymorphic markers | marker sequence | marker from another chromosome |

The ultimate utility of Digital Amplification lies in its ability to convert the intrinsically exponential nature of PCR to a linear one. It should thereby prove useful for experiments requiring the investigation of individual alleles, rare variants/mutations, or quantitative analysis of PCR products.

efficacy of therapy. Gene amplifications are characteristic of certain disease states. These can be measured using digital amplification. Alternatively spliced forms of a transcript can be detected and quantitated relative to other forms of the transcript using digital amplification on cDNA made from mRNA. Similarly, using cDNA made from mRNA one can determine relative levels of transcription of two different genes. One can use digital amplification to distinguish between a situation where one allele carries two mutations and one mutation is carried on each of two alleles in an individual. Allelic imbalances often result from a disease state. These can be detected using digital amplification.

Biological samples which can be used as the starting material for the analyses may be from any tissue or body sample from which DNA or mRNA can be isolated. Preferred sources include stool, blood, and lymph nodes. Preferably the biological sample is a cell-free lysate.

Molecular beacon probes according to the present invention can utilize any photoluminescent moiety as a detectable moiety. Typically these are dyes. Often these are fluorescent dyes. Photoluminescence is any process in which a material is excited by radiation such as light, is raised to an excited electronic or vibronic state, and subsequently re-emits that excitation energy as a photon of light. Such processes include fluorescence, which denotes emission accompanying descent from an excited state with paired electrons (a "singlet" state) or unpaired electrons (a "triplet" state) to a lower state with the same multiplicity, i.e., a quantum-mechanically "allowed" transition. Photoluminescence also includes phosphorescence which denotes emission accompanying descent from an excited triplet or singlet state to a lower state of different multiplicity, i.e., a quantum mechanically "forbidden" transition. Compared to "allowed" transitions, "forbidden" transitions are associated with relatively longer excited state lifetimes.

The quenching of photoluminescence may be analyzed by a variety of methods which vary primarily in terms of signal transduction. Quenching may be transduced as changes in the intensity of photoluminescence or as changes in the ratio of photoluminescence intensities at two different wavelengths, or as changes in photoluminescence lifetimes, or even as changes in the polarization (anisotropy) of photoluminescence. Skilled practitioners will recognize that instrumentation for the measurement of these varied photoluminescent responses are known. The particular ratiometric methods for the analysis of quenching in the instant examples should not be construed as limiting the invention to any particular form of signal transduction. Ratiometric measurements of photoluminescence intensity can include the measurement of changes in intensity, photoluminescence lifetimes, or even polarization (anisotropy).

Although the working examples demonstrate the use of molecular beacon probes as the means of analysis of the amplified dilution samples, other techniques can be used as well. These include sequencing, gel electrophoresis, hybridization with other types of probes, including TaqMan™ (dual-labeled fluorogenic) probes (Perkin Elmer Corp./Applied Biosystems, Foster City, Calif.), pyrene-labeled probes, and other biochemical assays.

The above disclosure generally describes the present invention. A more complete understanding can be obtained by reference to the following specific examples which are provided herein for purposes of illustration only, and are not intended to limit the scope of the invention.

Example 1

Step 1: PCR amplifications. The optimal conditions for PCR described in this section were determined by varying the parameters described in the Results. PCR was performed in 7 ul volumes in 96 well polypropylene PCR plates (RPI). The composition of the reactions was: 67 mM Tris, pH 8.8, 16.6 mM $NH_4SO_4$, 6.7 mM $MgCl_2$, 10 mM β-mercaptoethanol, 1 mM dATP, 1 mM dCTP, 1 mM dGTP, 1 mM TTP, 6% DMSO, 1 uM primer F1, 1 uM primer R1, 0.05 units/ul Platinum Taq polymerase (Life Technologies, Inc.), and "one-half genome equivalent" of DNA. To determine the amount of DNA corresponding to one-half genome equivalent, DNA samples were serially diluted and tested via PCR. The amount that yielded amplification products in half the wells, usually ~1 pg of total DNA, was defined as "one-half genome equivalent" and used in each well of subsequent Digital Amplification experiments. Fifty ul light mineral oil (Sigma M-3516) was added to each well and reactions performed in a HybAid Thermal cycler at the following temperatures: denaturation at 94° for one min; 60 cycles of 94° for 15 sec, 55° for 15 sec., 70° for 15 seconds; 70° for five minutes. Reactions were read immediately or stored at room temperature for up to 36 hours before fluorescence analysis.

Example 2

Step 2: Fluorescence analysis. 3.5 ul of a solution with the following composition was added to each well: 67 mM Tris, pH 8.8, 16.6 mM $NH_4SO_4$, 6.7 mM $MgCl_2$, 10 mM β-mercaptoethanol, 1 mM dATP, 1 mM dCTP, 1 mM dGTP, 1 mM TTP, 6% DMSO, 5 uM primer INT, 1 uM MB-GREEN, 1 uM MB-RED, 0.1 units/ul Platinum Taq polymerase. The plates were centrifuged for 20 seconds at 6000 g and fluorescence read at excitation/emission wavelengths of 485 nm/530 nm for MB-GREEN and 530 nm/590 nm for MB-RED. This fluorescence in wells without template was typically 10,000 to 20,000 fluorescence "units", with about 75% emanating from the fluorometer background and the remainder from the MB probes. The plates were then placed in a thermal cycler for asymmetric amplification at the following temperatures: 94° for one minute; 10-15 cycles of 94° for 15 sec, 55° for 15 sec., 70° for 15 seconds; 60° for five minutes. The plates were then incubated at room temperature for at least 20 minutes and fluorescence measured as described above. The fluorescence readings obtained were stable for several hours. Specific fluorescence was defined as the difference in fluorescence before and after the asymmetric amplification. RED/GREEN ratios were defined as the specific fluorescence of MB-RED divided by that of MB-GREEN. RED/GREEN ratios were normalized to the ratio exhibited by the positive controls (25 genome equivalents of DNA from normal cells, as defined in Materials and Methods). We found that the ability of MB probes to discriminate between WT and mutant sequences under our conditions could not be reliably determined from experiments in which they were tested by hybridization to relatively short complementary single stranded oligonucleotides, and that actual PCR products had to be used for validation.

Example 3

Oligonucleotides and DNA Sequencing.

Primer F1:
(SEQ ID NO: 1)
5'-CATGTTCTAATATAGTCACATTTTCA-3';

Primer R1:
(SEQ ID NO: 2)
5'-TCTGAATTAGCTGTATCGTCAAGG-3';

-continued

Primer INT:
(SEQ ID NO: 3)
5'-TAGCTGTATCGTCAAGGCAC-3';

MB-RED:
(SEQ ID NO: 4)
5'-Cy3-CACGGGCCTGCTGAAAATGACTGCGTG-Dabcyl-3';

MB-GREEN:
(SEQ ID NO: 5)
5'-Fluorescein-CACGGGAGCTGGTGGCGTAGCGTG-Dabcyl-3'..

Molecular Beacons were synthesized by Midland Scientific and other oligonucleotides were synthesized by Gene Link. All were dissolved at 50 uM in TE (10 mM Tris, pH 8.0/1 mM EDTA) and kept frozen and in the dark until use. PCR products were purified using QIAquick PCR purification kits (Qiagen). In the relevant experiments described in the text, 20% of the product from single wells was used for gel electrophoresis and 40% was used for each sequencing reaction. The primer used for sequencing was 5'-CATT-ATTTTTATTATAAGGCCTGC-3' (SEQ ID NO: 6). Sequencing was performed using fluorescently-labeled ABI Big Dye terminators and an ABI 377 automated sequencer.

Example 4

Principles underlying experiment. The experiment is outlined in FIG. 1A. First, the DNA is diluted into multiwell plates so that there is, on average, one template molecule per two wells, and PCR is performed. Second, the individual wells are analyzed for the presence of PCR products of mutant and WT sequence using fluorescent probes.

As the PCR products resulting from the amplification of single template molecules should be homogeneous in sequence, a variety of standard techniques could be used to assess their presence. Fluorescent probe-based technologies, which can be performed on the PCR products "in situ" (i.e., in the same wells) are particularly well-suited for this application. We chose to explore the utility of one such technology, involving Molecular Beacons (MB), for this purpose. MB probes are oligonucleotides with stem-loop structures that contain a fluorescent dye at the 5' end and a quenching agent (Dabcyl) at the 3' end (FIG. 1B). The degree of quenching via fluorescence energy resonance transfer is inversely proportional to the $6^{th}$ power of the distance between the Dabcyl group and the fluorescent dye. After heating and cooling, MB probes reform a stem-loop structure which quenches the fluorescent signal from the dye. If a PCR product whose sequence is complementary to the loop sequence is present during the heating/cooling cycle, hybridization of the MB to one strand of the PCR product will increase the distance between the Dabcyl and the dye, resulting in increased fluorescence.

A schematic of the oligonucleotides used for Digital Amplifications shown in FIG. 1C. Two unmodified oligonucleotides are used as primers for the PCR reaction. Two MB probes, each labeled with a different fluorophore, are used to detect the PCR products. MB-GREEN has a loop region that is complementary to the portion of the WT PCR product that is queried for mutations. Mutations within the corresponding sequence of the PCR product should significantly impede the hybridization of it to the MB probe. MB-RED has a loop region that is complementary to a different portion of the PCR product, one not expected to be mutant. It thus should produce a signal whenever a well contains a PCR product, whether that product is WT or mutant in the region queried by MB-GREEN. Both MB probes are used together to simultaneously detect the presence of a PCR product and its mutational status.

Practical Considerations.

Numerous conditions were optimized to define conditions that could be reproducibly and generally applied. As outlined in FIG. 1A, the first step involves amplification from single template molecules. Most protocols for amplification from small numbers of template molecules use a nesting procedure, wherein a product resulting from one set of primers is used as template in a second reaction employing internal primers. As many applications of digital amplification are expected to require hundreds or thousands of separate amplifications, such nesting would be inconvenient and could lead to contamination problems. Hence, conditions were sought that would achieve robust amplification without nesting. The most important of these conditions involved the use of a polymerase that was activated only after heating and optimized concentrations of dNTP's, primers, buffer components, and temperature. The conditions specified in Examples 1-3 were defined after individually optimizing each of these components and proved suitable for amplification of several different human genomic DNA sequences. Though the time required for PCR was not particularly long (~2.5 hr), the number of cycles used was high and excessive compared to the number of cycles required to amplify the "average" single template molecule. The large cycle number was necessary because the template in some wells might not begin to be amplified until several PCR cycles had been completed. The large number of cycles ensured that every well (not simply the average well) would generate a substantial and roughly equal amount of PCR product if a template molecule were present within it.

The second step in FIG. 1A involves the detection of these PCR products. It was necessary to considerably modify the standard MB probe approach in order for it to function efficiently in Digital Amplification applications. Theoretically, one separate MB probe could be used to detect each specific mutation that might occur within the queried sequence. By inclusion of one MB corresponding to WT sequence and another corresponding to mutant sequence, the nature of the PCR product would be revealed. Though this strategy could obviously be used effectively in some situations, it becomes complex when several different mutations are expected to occur within the same queried sequence. For example, in the c-Ki-Ras gene example explored here, twelve different base substitutions resulting in missense mutations could theoretically occur within codons 12 and 13, and at least seven of these are observed in naturally-occurring human cancers. To detect all twelve mutations as well as the WT sequence with individual Molecular Beacons would require 13 different probes. Inclusion of such a large number of MB probes would not only raise the background fluorescence but would be expensive. We therefore attempted to develop a single probe that would react with WT sequences better than any mutant sequence within the queried sequence. We found that the length of the loop sequence, its melting temperature, and the length and sequence of the stem were each important in determining the efficacy of such probes. Loops ranging from 14 to 26 bases and stems ranging from 4 to 6 bases, as well as numerous sequence variations of both stems and loops, were tested during the optimization procedure. For discrimination between WT and mutant sequences (MB-GREEN probe), we found that a 16 base pair loop, of melting temperature (Tm) 50-51°, and a 4 bp stem, of sequence 5'-CACG-3', were optimal. For MB-RED probes, the same stem, with a 19-20 bp loop of Tm 54-56°, proved optimal. The differences in the loop sizes and melting temperatures between MB-GREEN and MB-RED probes reflected the fact that only the GREEN probe is designed to discriminate between closely related sequences, with a shorter region of homology facilitating such discrimination.

Examples of the ratios obtained in replicate wells containing DNA templates from colorectal tumor cells with mutations of c-Ki-Ras are shown in FIG. 2. In this experiment, fifty copies of genomic DNA equivalents were diluted into each well prior to amplification. Each of six tested mutants yielded ratios of RED/GREEN fluorescence that were significantly in excess of the ratio obtained with DNA from normal cells (1.5 to 3.4 in the mutants compared to 1.0 in normal DNA; p<0.0001 in each case, Student's t-Test). The reproducibility of the ratios can be observed in this figure. Direct DNA sequencing of the PCR products used for fluorescence analysis showed that the RED/GREEN ratios were dependent on the relative fraction of mutant genes within the template population (FIG. 2). Thus, the DNA from cells containing one mutant C-Ki-Ras allele per every two WT c-Ki-Ras allele yielded a RED/GREEN ratio of 1.5 (Gly12Arg mutation) while the cells containing three mutant c-Ki-Ras alleles per WT allele exhibited a ratio of 3.4 (Gly12Asp). These data suggested that wells containing only mutant alleles (no WT) would yield ratios in excess of 3.0, with the exact value dependent on the specific mutation.

Though this mode is the most convenient for many applications, we found it useful to add the MB probes after the PCR-amplification was complete (FIG. 1). This allowed us to use a standard multiwell plate fluorometer to sequentially analyze a large number of multiwell plates containing pre-formed PCR products and bypassed the requirement for multiple real time PCR instruments. Additionally, we found that the fluorescent signals obtained could be considerably enhanced if several cycles of asymmetric, linear amplification were performed in the presence of the MB probes. Asymmetric amplification was achieved by including an excess of a single internal primer (primer INT in FIG. 1C) at the time of addition of the MB probes.

Example 5

Figure 4:
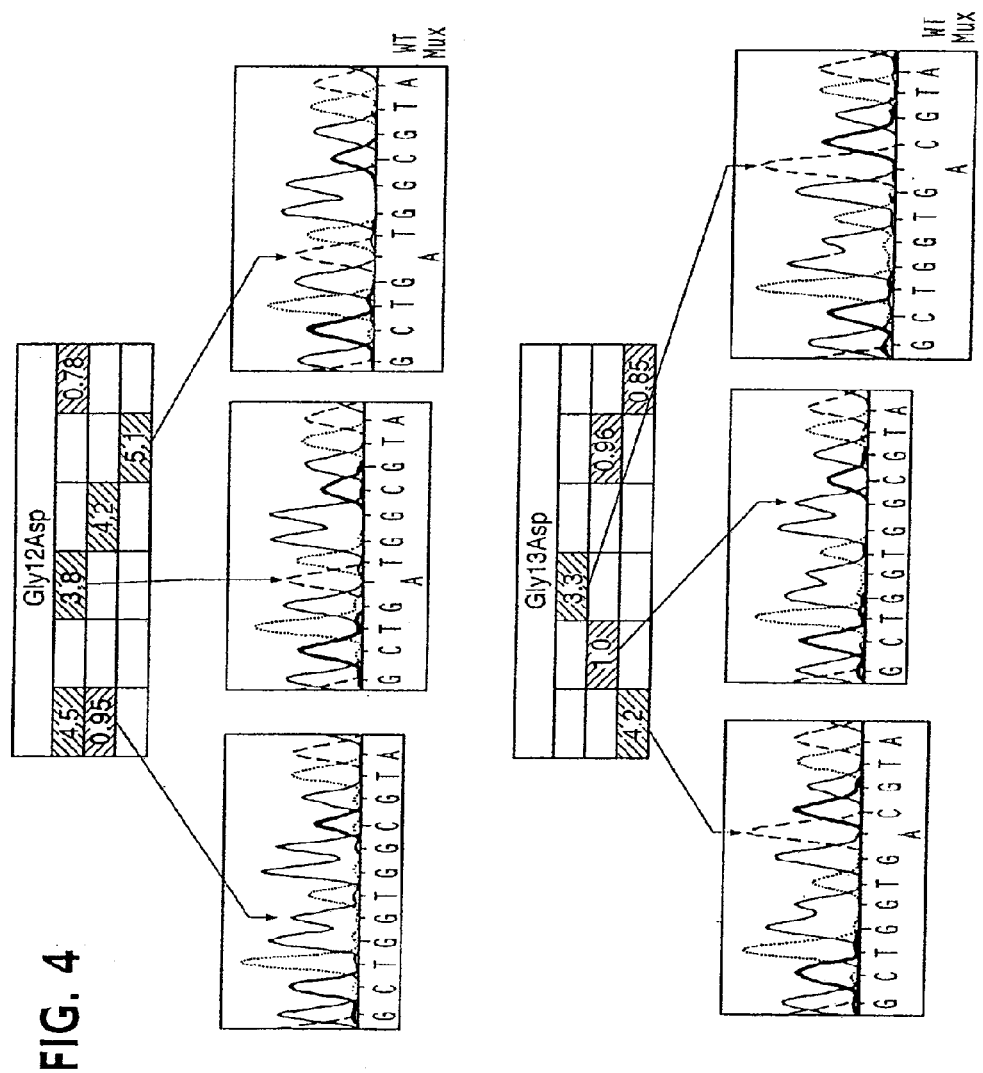
FIG. 4. Discriminating WT from mutant PCR products obtained in Dig-PCR. RED/GREEN ratios were determined from the fluorescence of MB-RED and MB-GREEN as described in Materials and Methods. The wells shown are the same as those illustrated in FIG. 3. The sequences of PCR products from the indicated wells were determined as described in Materials and Methods. The wells with RED/GREEN ratios >3.0 each contained mutant sequences while those with RED/GREEN ratios of ~1.0 contained WT sequences. WT c-Ki-Ras (SEQ ID NO: 7), Gly12Asp (SEQ ID NO: 13), and Gly13Asp (SEQ ID NO: 9) were analyzed.

Analysis of DNA from tumor cells. The principles and practical considerations described above was demonstrated with DNA from two colorectal cancer cell lines, one with a mutation in c-Ki-Ras codon 12 and the other in codon 13. Representative examples of the MB-RED fluorescence values obtained are shown in FIG. 3. There was a clear biphasic distribution, with "positive" wells yielding values in excess of 10,000 specific fluorescence units (SFU, as defined in Materials and Methods) and "negative" wells yielding values less than 3500 SFU. Gel electrophoreses of 127 such wells demonstrated that all positive wells, but no negative wells, contained PCR products of the expected size (FIG. 3). The RED/GREEN fluorescence ratios of the positive wells are shown in FIG. 4. Again, a biphasic distribution was observed. In the experiment with the tumor containing a Gly12Asp mutation, 64% of the positive wells exhibited RED/GREEN ratios in excess of 3.0 while the other 36% of the positive wells exhibited ratios ranging from 0.8 to 1.1. In the case of the tumor with the Gly13Asp mutation, 54% of the positive wells exhibited RED/GREEN ratios >3.0 while the other positive wells yielded ratios ranging from 0.9 to 1.1. The PCR products from 16 positive wells were used as sequencing templates (FIG. 4). All the wells yielding a ratio in excess of 3.0 were found to contain mutant c-Ki-Ras fragments of the expected sequence, while WT sequence was found in the other PCR products. The presence of homogeneous WT or mutant sequence confirmed that the amplification products were usually derived from single template molecules. The ratios of WT to mutant PCR products determined from the Digital Amplification assay was also consistent with the fraction of mutant alleles inferred from direct sequence analysis of genomic DNA from the two tumor lines (FIG. 2).

Figure 5:
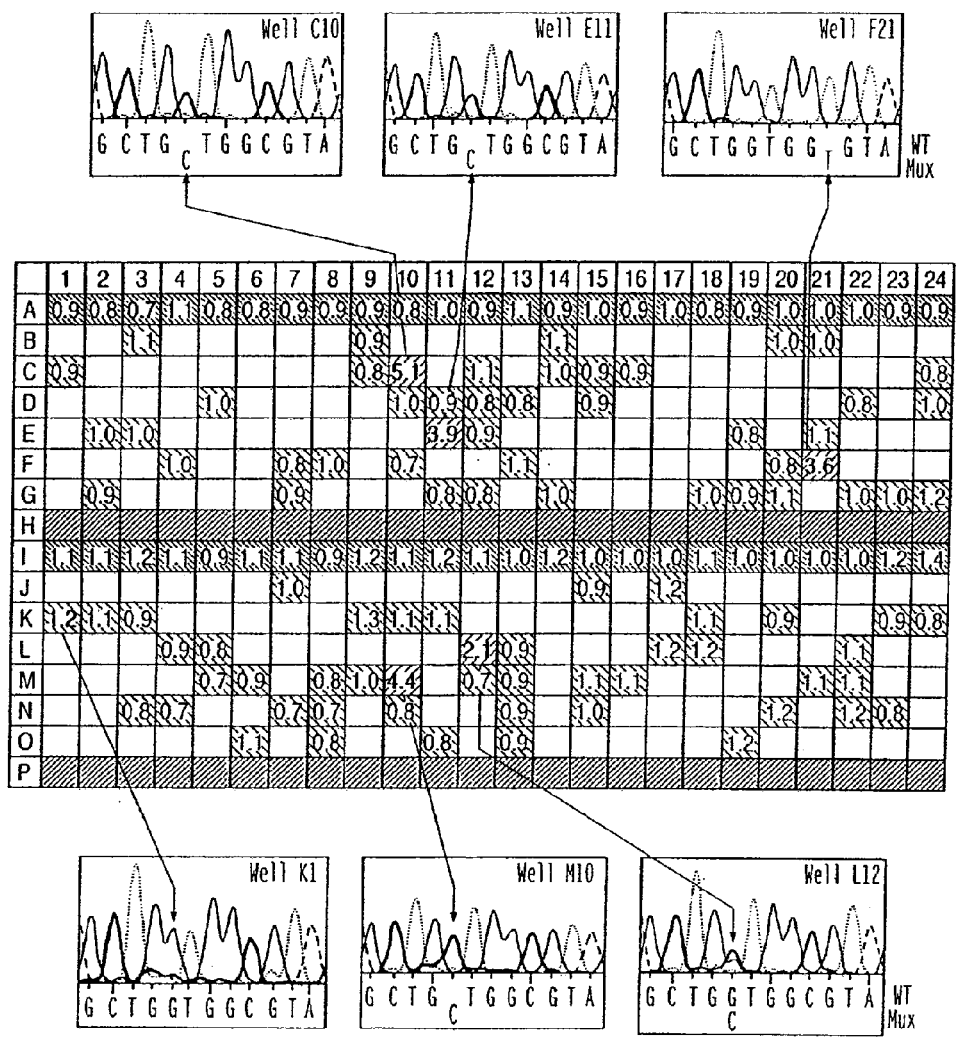
FIG. 5. Dig-PCR of DNA from a stool sample. The 384 wells used in the experiment are displayed. Those colored blue contained 25 genome equivalents of DNA from normal cells. Each of these registered positive with MB-RED and the RED/GREEN ratios were 1.0+/−0.1 (mean+/−1 standard deviation). The wells colored yellow contained no template DNA and each was negative with MB-RED (i.e., fluorescence <3500 fluorescence units.). The other wells contained diluted DNA from the stool sample. Those registering as positive with MB-RED were colored either red or green, depending on their RED/GREEN ratios. Those registering negative with MB-RED were colored white. PCR products from the indicated wells were used for automated sequence analysis. The sequence of WT c-Ki-Ras in well (SEQ ID NO: 7), and mutant c-Ki-Ras in wells C10, E11, M10, and L12 (SEQ ID NO: 14), and well F21 (SEQ ID NO: 15) were analyzed.

Digital Analysis of DNA from stool. As a more practical example, we analyzed the DNA from stool specimens from colorectal cancer patients. A representative result of such an experiment is illustrated in FIG. 5. From previous analyses of stool specimens from patients whose tumors contained c-Ki-Ras gene mutations, we expected that 1% to 10% of the c-Ki-Ras genes purified from stool would be mutant. We therefore set up a 384 well Digital Amplification experiment. As positive controls, 48 of the wells contained 25 genome equivalents of DNA (defined in Materials and Methods) from normal cells. Another 48 wells served as negative controls (no DNA template added). The other 288 wells contained an appropriate dilution of stool DNA. MB-RED fluorescence indicated that 102 of these 288 experimental wells contained PCR products (mean+/−s.d. of 47,000+/−18,000 SFU) while the other 186 wells did not (2600+/−1500 SFU). The RED/GREEN ratios of the 102 positive wells suggested that five contained mutant c-Ki-Ras genes, with ratios ranging from 2.1 to 5.1. The other 97 wells exhibited ratios ranging from 0.7 to 1.2, identical to those observed in the positive control wells. To determine the nature of the mutant c-Ki-Ras genes in the five positive wells from stool, the PCR products were directly sequenced. The four wells exhibiting RED/GREEN ratios in excess of 3.0 were completely composed of mutant c-Ki-Ras sequence (FIG. 5B). The sequence of three of these PCR products revealed Gly12Ala mutations (GGT to GCT at codon 12), while the sequence of the fourth indicated a silent C to T transition at the third position of codon 13. This transition presumably resulted from a PCR error during the first productive cycle of amplification from a WT template. The well with a ratio of 2.1 contained a ~1:1 mix of WT and Gly12Ala mutant sequences. Thus 3.9% (4/102) of the c-Ki-Ras alleles present in this stool sample contained a Gly12Ala mutation. The mutant alleles in the stool presumably arose from the colorectal cancer of the patient, as direct sequencing of PCR products generated from DNA of the cancer revealed the identical Gly12Ala mutation (not shown).

We claim:

1. A method for detecting an imbalance in a mixed population of human genomic nucleic acid sequences, comprising:

distributing a mixed population of cell-free, human genomic nucleic acid template molecules from a sample into a set comprising at least fifteen assay samples such that said at least fifteen assay samples each comprises less than ten template molecules, wherein the mixed population comprises at least a first and a second human genomic sequence, wherein the first sequence is on a first chromosome and the second sequence is on a second chromosome;

amplifying the template molecules in the assay samples, wherein an assay sample with a single template molecule forms homogeneous amplification products in the assay sample;

analyzing by determining nucleic acid sequence of amplification products in the assay samples of the set to determine a first number of assay samples in the set which contain the first human genomic sequence and a second number of assay samples in the set which contain the second human genomic sequence;

comparing the first number to the second number to determine an imbalance in the mixed population between the first and the second chromosomes.

2. The method of claim 1 wherein the set comprises at least 500 assay samples.

3. The method of claim 1 wherein the set comprises at least 1000 assay samples.

4. The method of claim 1 wherein the amplified molecules in each of the assay samples within the first and second numbers of assay samples are homogeneous such that the first number of assay samples do not contain the second human genomic sequence and the second number of assay samples do not contain the first human genomic sequence.

5. The method of claim 1 wherein the distributing is performed by diluting.

6. The method of claim 1 wherein the biological sample is from blood.

7. The method of claim 1 wherein the first human genomic sequence is a non-polymorphic marker.

8. The method of claim 1 wherein the mixed population of nucleic acid template molecules is distributed such that at least one thousand assay samples are distributed to a single template molecule level.

9. The method of claim 1 wherein the mixed population of nucleic acid template molecules is distributed such that at least one thousand assay samples each comprise less than ten template molecules.

10. The method of claim 1 wherein the mixed population of nucleic acid template molecules is distributed such that at least five hundred assay samples each comprise less than ten template molecules.

11. The method of claim 1 wherein the mixed population of nucleic acid template molecules is distributed such that at least one hundred assay samples each comprise less than ten template molecules.

* * * * *

UNITED STATES PATENT AND TRADEMARK OFFICE
CERTIFICATE OF CORRECTION

| | | |
|---|---|---|
| PATENT NO. | : 9,970,058 B2 | Page 1 of 1 |
| APPLICATION NO. | : 14/512694 | |
| DATED | : May 15, 2018 | |
| INVENTOR(S) | : Bert Vogelstein and Kenneth W. Kinzler | |

It is certified that error appears in the above-identified patent and that said Letters Patent is hereby corrected as shown below:

In the Specification

Column 1, Lines 1-4, replace:
"The U.S. government retains certain rights in this invention by virtue of its support of the underlying research, supported by grants CA 43460, CA 57345, and CA 62924 from the National Institutes of Health."
With:
-- STATEMENT OF FEDERALLY SPONSORED RESEARCH
This invention was made with government support under Grant no. CA43460, CA57345, and CA62924, awarded by the National Institutes of Health. The government has certain rights in the invention. --

Signed and Sealed this
Twenty-eighth Day of April, 2020

Andrei Iancu
*Director of the United States Patent and Trademark Office*

SEQUENCE LISTING

<160> NUMBER OF SEQ ID NOS: 15

<210> SEQ ID NO 1
<211> LENGTH: 26
<212> TYPE: DNA

<213> ORGANISM: homo sapiens

<400> SEQUENCE: 1
catgttctaa tatagtcaca ttttca                                          26

<210> SEQ ID NO 2
<211> LENGTH: 24
<212> TYPE: DNA
<213> ORGANISM: homo sapiens

<400> SEQUENCE: 2
tctgaattag ctgtatcgtc aagg                                            24

<210> SEQ ID NO 3
<211> LENGTH: 20
<212> TYPE: DNA
<213> ORGANISM: homo sapiens

<400> SEQUENCE: 3
tagctgtatc gtcaaggcac                                                 20

<210> SEQ ID NO 4
<211> LENGTH: 27
<212> TYPE: DNA
<213> ORGANISM: homo sapiens

<400> SEQUENCE: 4
cacgggcctg ctgaaaatga ctgcgtg                                         27

<210> SEQ ID NO 5
<211> LENGTH: 24
<212> TYPE: DNA
<213> ORGANISM: homo sapiens

<400> SEQUENCE: 5
cacgggagct ggtggcgtag cgtg                                            24

<210> SEQ ID NO 6
<211> LENGTH: 24
<212> TYPE: DNA
<213> ORGANISM: homo sapiens

<400> SEQUENCE: 6
cattattttt attataaggc ctgc                                            24

<210> SEQ ID NO 7
<211> LENGTH: 12
<212> TYPE: DNA
<213> ORGANISM: homo sapiens

<400> SEQUENCE: 7
gctggtggcg ta                                                         12

<210> SEQ ID NO 8
<211> LENGTH: 12
<212> TYPE: DNA
<213> ORGANISM: homo sapiens

<400> SEQUENCE: 8
gctagtggcg ta                                                         12

<210> SEQ ID NO 9
<211> LENGTH: 12

-continued

```
<212> TYPE: DNA
<213> ORGANISM: homo sapiens

<400> SEQUENCE: 9
gctggtgacg ta                                                    12

<210> SEQ ID NO 10
<211> LENGTH: 12
<212> TYPE: DNA
<213> ORGANISM: homo sapiens

<400> SEQUENCE: 10
gctcgtggcg ta                                                    12

<210> SEQ ID NO 11
<211> LENGTH: 13
<212> TYPE: DNA
<213> ORGANISM: homo sapiens

<400> SEQUENCE: 11
gcttgtggcc gta                                                   13

<210> SEQ ID NO 12
<211> LENGTH: 13
<212> TYPE: DNA
<213> ORGANISM: homo sapiens

<400> SEQUENCE: 12
gctgatgggc gta                                                   13

<210> SEQ ID NO 13
<211> LENGTH: 12
<212> TYPE: DNA
<213> ORGANISM: homo sapiens

<400> SEQUENCE: 13
gctgatggcg ta                                                    12

<210> SEQ ID NO 14
<211> LENGTH: 12
<212> TYPE: DNA
<213> ORGANISM: homo sapiens

<400> SEQUENCE: 14
gctgctggcg ta                                                    12

<210> SEQ ID NO 15
<211> LENGTH: 12
<212> TYPE: DNA
<213> ORGANISM: homo sapiens

<400> SEQUENCE: 15
gctggtggtg ta                                                    12
```